United States Patent [19]
Alt et al.

[11] Patent Number: 6,159,237
[45] Date of Patent: Dec. 12, 2000

[54] IMPLANTABLE VASCULAR AND ENDOLUMINAL STENTS

[75] Inventors: Eckhard Alt, Ottobrunn; Thilo Fliedner; Robert Alter, both of Munich; Axel Stemberger, Neubiberg, all of Germany

[73] Assignee: Inflow Dynamics, Inc., Wilmington, Del.

[21] Appl. No.: 09/186,573

[22] Filed: Nov. 5, 1998

Related U.S. Application Data

[63] Continuation of application No. 08/599,880, Feb. 14, 1996, Pat. No. 5,843,117.

[51] Int. Cl.$^7$ ........................................................ A61F 2/06
[52] U.S. Cl. .......................................... 623/1.11; 623/1.15
[58] Field of Search ................................... 606/108, 198, 606/191, 195; 623/1, 12, 901, 1.11, 1.15

[56] References Cited

U.S. PATENT DOCUMENTS

| | | | |
|---|---|---|---|
| 3,868,956 | 3/1975 | Alfidi et al. | 606/194 |
| 5,304,200 | 4/1994 | Spaulding | 606/195 X |
| 5,330,483 | 7/1994 | Heaven et al. | 606/114 |
| 5,370,683 | 12/1994 | Fontaine | 623/1 |
| 5,397,355 | 3/1995 | Marin et al. | 623/12 |
| 5,409,495 | 4/1995 | Osborn | 606/108 |
| 5,449,373 | 9/1995 | Pinchasik et al. | 606/198 |
| 5,514,154 | 5/1996 | Lau et al. | 600/108 |
| 5,514,176 | 5/1996 | Bosley et al. | 623/1 |
| 5,591,197 | 1/1997 | Orth et al. | 606/198 |
| 5,591,230 | 1/1997 | Horn et al. | 623/1 X |
| 5,593,442 | 1/1997 | Klein | 623/12 |
| 5,607,463 | 3/1997 | Schwartz et al. | 623/1 |
| 5,632,760 | 5/1997 | Sheiban et al. | 606/191 |
| 5,645,559 | 7/1997 | Hachtman et al. | 606/198 |
| 5,649,951 | 7/1997 | Davidson | 606/198 |
| 5,649,977 | 7/1997 | Campbell | 606/195 X |

Primary Examiner—Michael H. Thaler

[57] ABSTRACT

A vascular or endoluminal stent adapted for deployment in a vessel or tract of a patient to maintain an open lumen therein is formed from a metal open-ended tube which is the single component of the stent. The tube has a multiplicity of holes cut by laser through its wall. The through-holes are encompassed by serpentines that constitute the wall, the serpentines extending sinusoidally each in multiple 360° wavelengths in a single turn about the axis of the tube and juxtaposed in plural substantially identical segments disposed with regularity along the axis. Each segment has a length equal to the distance between crests and troughs of the sinusoid. Adjacent serpentines are joined together at crest and trough, respectively, so that their interconnections are 180° out of phase relative to their wavelength. The serpentines and interconnections thereof are shaped throughout for optimum uniform expansion of the stent during deployment thereof including a notch substantially symmetrically located at either side of the junction of the respective crest and trough of the interconnections between adjacent serpentines. The serpentines are substantially devoid of sharp corners and edges, except at the notches, and each serpentine has an oval cross-section. The regularity of the segments is interrupted at least once along the axis of the tube by serpentines oriented differently from the others, used to maintain the tube's length substantially invariant despite radial expansion of the stent during deployment. The serpentines are pre-stressed and annealed before deployment of the stent to ease deployment and enhance symmetrical radial expansion. The exterior surface of the tube is longitudinally tapered from its mid-point toward its ends, and substantially rounded surfaces prevail throughout the tube.

16 Claims, 3 Drawing Sheets

IMPLANTABLE VASCULAR AND ENDOLUMINAL STENTS

CROSS-REFERENCE TO RELATED APPLICATION

This application is a continuation of application Ser. No. 08/599,880 filed Feb. 14, 1996 of the same applicants and same assignee, now U.S. Pat. No. 5,843,117, the priority date of which is hereby claimed for this application.

BACKGROUND OF THE INVENTION

The present invention relates generally to stents which are implantable or deployable in a vessel or duct within the body of a patient to maintain the lumen of the duct or vessel open, and more particularly to improvements in stent structures, stenting procedures, and processes for making stents.

Stents are expandable vascular and endoluminal prostheses, usually employed to keep a particular site in the blood vessels open and unoccluded, especially in the coronary and femoral arteries, following treatment such as dilatation by balloon catheter angioplasty. But these devices are also quite useful in other applications as well, such as in other tracts internally of the human body where an aid is required at a target site to maintain the lumen open and unobstructed. Examples are the tracheo-bronchial system, the biliary hepatic system, the esophageal bowel system, and the urinary tract system. In general, a vascular stent in particular must be sufficiently dimensionally stable to keep the vessel and lumen open while resisting recoil of its elastic wall that naturally occurs when the site within the vessel or luminal structure has been subjected to outwardly directed forces that are necessary to expand the elastic fibers, compress fatty deposits on the wall, and/or to deploy the stent, and to prevent an acute closure following dissection of the vessel.

In practice thus far, two types of stents have predominated for clinical vascular applications. One type, exemplified by a stent available from Cordis Corporation, is fabricated from a round wire laid into a zig-zag form, described more fully in U.S. Pat. No. 4,580,568. The other type is referred to as the Palmaz-Schatz stent, manufactured from a longitudinal tubular element with a narrow central lumen, as described in European Patent EP 81-0221570. In the Palmaz-Schatz type, the longitudinal metal tubular element is open at both ends and has rectangularly shaped, longitudinally oriented openings in its wall that form a pattern of confluent intersecting struts.

These wire and tubular stents, as well as other types, are expanded to a larger diameter by application of radial forces directed outwardly from within the lumen of the stent by inflation of a precision expansion balloon of a catheter on which the stent is mounted. Typically, the balloon is coupled for inflation at the distal end of a catheter that may have several lumens, such as to permit blood perfusion, guide wire (rail) advancement, and other purposes, as well as for pressurizing (inflating) and de-pressurizing (deflating) the balloon.

In the case of a wire stent, such as that of the '568 patent, although the wire has a round cross section with relatively low risk of causing significant injury to the vessel wall, it makes only line contact with the wall at each wire segment. More importantly, this type of stent lacks the radial strength to resist forces of compression, and thus, is unable to withstand elastic recoil of the vessel wall following expansion thereof such as after balloon angioplasty. As a result, a wire stent may suffer a loss in lumen diameter in the vessel of up to about 30%. For example, the wall of a vessel whose lumen has been expanded by balloon inflation to a diameter of 4 millimeters (mm) can undergo recoil within days to a diameter of 3 mm, despite implantation of a wire stent.

The Palmaz-Schatz stent described in the EP 81-0221570 patent has a relatively stiff structure with good resistance to compression, and therefore, the dimensional stability to resist the vessel wall's elastic recoil and maintain lumen diameter. But it has the disadvantage of presenting greater risk of injury to the vessel wall or damage to its expansion balloon because of sharp edges. Clinical practice and animal experiments have demonstrated that the sharp edges of individual struts of this type of stent can cut into the medial and intimal layers of the vessel wall. With typical stent wall thickness in the range from 65 to 100 microns, its edges are almost knife-like. A deep cut in the vessel wall from such an edge during deployment of the stent can signal disaster. Even minor scraping or other abrasion of the vessel wall from these edges or protuberances provoke the healing phenomena of smooth muscle cell hyperplasia, which leads to restenosis. Recent clinical data has shown also that the restenosis rate with this type of stent is in the range of from 25% to 35%, which lessens its advantage of rigidity against radial compression.

Also, since the stent is crimped onto an uninflated balloon of a balloon catheter for subsequent deployment, any sharp edges are prone to puncture or rupture the balloon at that time or during stent advancement through the vessel or during deployment. If the balloon cannot be inflated to the size necessary to properly deploy the stent because the membrane has ruptured or is lealdng, and so leaves the stent either unopened or only partly opened, it may not be possible to retract the stent. In that case, the stent will remain in the blood vessel as an unuseful foreign body, incapable of maintaining an open lumen, and possibly to ultimately cause complete blockage of the vessel. If that were to occur in a coronary artery, it could lead to myocardial infarction, and potentially, death of the patient. In the case of loss of the stent in a femoral artery, the result could also be total obstruction and result in a significant compromise of leg blood circulation. We have observed clinical procedures where the balloon ruptured because of the stent's sharp edges when the inflation pressure exceeded three atmospheres.

Moreover, because the target site in the vessel is often deep within the vessel or body of the patient, with the necessity to advance the stent on its balloon catheter through a long, often tortuous path of normal or diseased vessel, the likelihood increases that sharp edges of the stent will cut into arterial tissue and provoke an acute closure, or compromise or prevent advancement of the stent to the target site. Here again, then, the stent must be adapted to enable it be advanced on the balloon catheter in relatively smooth, unimpeded fashion through the vessel lumen to the predetermined target site a which it is to be deployed.

It is also imperative that the stent will expand radially and reliably in a symmetric manner in response to the forces exerted on its interior surface by the inflating balloon. Several studies conducted by the applicants have shown that existing tube type stents all too often expand asymmetrically, despite application of homogeneous radial forces by the expansion balloon. We have found that a significant part of this problem is that a considerable initial force is required to induce primary bending of the struts (i.e., to overcome structural inertia), so as to displace them from initial positions primarily parallel to one another into a more net-like or rhombic position. This initial force is higher than that required for further expansion of the stent to a fully deployed position.

Typically, at least a few of the struts of the most popular existing tube type stents remain in their parallel or substantially parallel original positions during deployment of the stent, thereby forcing other struts to undergo overexpansion with ongoing inflation of the expansion balloon, which causes asymmetric opening of the stent. The result is that some of the through holes in wall of the stent grow much larger than others, which lends them to accommodate inward protrusion of the vessel wall, impeding blood flow and causing turbulent in the region of the target or implant site. Ironically, this tends to induce restenosis which the stent was implanted to prevent.

Several clinical investigations have focused on ways to assure symmetrical radial expansion of the stent. For example, reliable symmetric opening has been sought by use of a high pressure balloons, inflatable to pressures ranging from 12 to 20 atmospheres. But this has several drawbacks, such as requiring the use of a second balloon (the high pressure balloon) at the target site, and causing additional trauma to the vessel wall which may include tearing and dissectioning that induces restenosis. A study recently completed at our clinic has shown that late lumen loss is proportionately greater when higher inflation forces are used to deploy the stent. Moreover, high pressure balloons are expensive (present-day cost ranges from about $600 to $1,000 per balloon), and like others, are not reusable.

Restenosis can originate not only at openings within the stent but at either or both of its ends where a transition exists in the lumen, from a stiff metal prosthesis to a very elastic vessel wall. At the transition region, considerable mechanical bending force is applied to the vessel wall by the presence of the stent—prompting a vascular reaction that leads to restenosis.

Although wire type stents, being more flexible, are less likely to cause this problem, they have the aforementioned inability to withstand vessel recoil. Moreover, the inadequate support of the diseased vessel wall offered by wire stents has been shown by many dissections. Wire tends to provide line support, which is inferior to the support given by the thicker, rectangular shapes typically found in the tube type stents. Wire meshes, like asymmetrically expanded tube type stents, can have very large holes that encourage inward protrusion of the vessel wall, with the same undesirable results.

All too frequently, the bending that occurs during expansion of known tube type stents causes twisting or torquing of at least some of their elongate strut members. In some instances, the twisting is attributable to weakness in the structure at locations where the struts are connected by bridges or bars of thicker or thinner cross-section, or where other regions of non-uniform thickness exist. When the struts become twisted, the vessel wall will be engaged by the stent, at least partly by the edge of the thin-walled (e.g., 65–70 microns thick) tubing, instead of the wider (e.g., 140 microns) side of the strut, with the aforementioned results of tissue or balloon membrane damage.

Also, if the physician finds it necessary to insert a balloon-mounted stent through an already-deployed stent, the order of difficulty is considerably greater where the latter has a twisted structure since it creates a region of higher friction in the lumen. This increases the possibility that the edge of the stent being deployed will become hooked distally of the existing implanted stent. The problem can occur where the site of a dissection to be stented was inadequately identified by dye, so that incomplete coverage is afforded by the stent now implanted, leaving a distally unsupported dissected region. Within a short time, typically from 5 to 15 minutes, the unstable vessel wall condition and the need to place a second stent distally of the first will become visually apparent.

It is a principal aim of the present invention to provide a stent which is less likely than those of the prior art to injure the vessel or tract wall during advancement through the lumen thereof, or to rupture the membrane of the balloon during initial mounting or subsequently while advancing or inflating the balloon for deployment, which requires less force for expansion and which expands symmetrically, and provides better protection against restenosis.

SUMMARY OF THE INVENTION

According to the invention, a vascular or endoluminal stent includes a biocompatible hollow open-ended tube as the single member from which the entire stent is fabricated, and a multiplicity of openings through the wall of the tube shaped according to a plurality of serpentine elements in the wall that run circumferentially in juxtaposed substantially sine wave-like patterns. All patterns are of uniform multiple cycles, with adjacent ones of them offset from each other by a predetermined phase difference at interconnecting points between them about the circumference of the tubular wall. The patterns are uniformly displaced longitudinally along the axis of the tube.

The phase difference at interconnecting points between adjacent longitudinally-displaced sine wave-like patterns of the serpentine elements is 180°, viewed as the offset between cyclical waves of the two, and each of the interconnecting points includes means in the form of circumferential notches between them to enhance crimping and symmetric expansion of the stent on a balloon, or means otherwise adapted to exert relatively uniform radial outwardly-directed forces from within the tube. Each of the serpentine elements has a rounded cross-section, in particular an oval cross-section. The uniform longitudinal displacement of the circumferential sine wave-like patterns is interrupted at least once along the stent's axis by transversely oriented serpentine elements that run longitudinally within the tube wall in juxtaposed at least partial sine wave-like patterns, and that serve to shape openings through the wall between them. Adjacent transverse patterns are offset from each other by a 180° cyclical phase difference at interconnecting points between them along the tube's axis. These transversely oriented serpentine elements are adapted to maintain the length of the tube substantially invariant with radial expansion of the stent.

In the stent, the phase difference at the interconnecting points between adjacent longitudinally-displaced ones of the sine wave-like patterns of the serpentine elements may alternatively be viewed as being less than 180° relative to the 360° circumference of the tube and the number of sine wave-like cycles in each of the circumferential patterns.

The tube, as structured with the serpentine elements and openings, is annealed, and has longitudinally tapered ends to more easily traverse the tortuous path typically encountered by the stent as it is advanced through the human vascular system to the target site at which the stent is to be deployed. Preferably, the wall of the tube is laser cut to cleanly form the openings and serpentine elements therein. Also, the tube is adapted for symmetric expansion of the stent by being pre-opened from its original production diameter to a second larger diameter which still falls well short of its fully deployed diameter on radial expansion.

The stent tube has substantially rounded surfaces throughout, except at the notched points, and the transverse patterns are adapted to maintain the length of the tube substantially invariant during radial expansion of the stent. An expansion balloon may be inserted into the axial lumen of the tube so that the proximal and distal ends of the balloon extend beyond the proximal and distal ends of the stent, and the stent then affixed to the balloon by partial inflation thereof. A catheter shaft connected to the proximal end of the balloon has a lumen for inflation of the balloon, and enables advancement of the stent on the partially inflated balloon in a vessel or tract of the patient to the target site, and enables deployment of the stent by further inflation of the balloon at the site. In essence, the balloon is inflated to a pressure in the range from 0.1 to 0.5 atmospheres, to distend the balloon sufficiently at the portions of its distal and proximal ends which extend beyond the respective ends after the stent is crimped on the balloon. The crimped stent is thereby retained firmly in place on the balloon and a cushion is created for protecting the stent and preventing it from contacting tissue during advancement through the vessel or tract to the target site. The tube is mechanically biased to substantially reduce inertial forces needed to be overcome to enable substantially symmetrical expansion of the stent during its deployment.

In another respect, the stent of the invention may be viewed as a metal open-ended ended tube with a multiplicity of through holes in its wall encompassed by serpentines that constitute the wall, the serpentines extending sinusoidally each in multiple 360° wavelengths in a single turn about the axis of the tube and juxtaposed in plural substantially identical segments disposed with regularity along the axis. Each segment has a length equal to the distance between crests and troughs of the sinusoid, and adjacent serpentines are joined together at crest and trough, respectively, to be interconnected 180° out of phase relative to the wavelength of the immediately adjacent sinusoid. The tube is the single component of the stent, and its serpentines and interconnections are shaped throughout for optimum uniform expansion of the stent during deployment.

A process of fabricating such a stent includes cutting through a metal open-ended tube to form a multiplicity of through holes in the tube wall, encompassed by the serpentines that constitute the wall. The cutting produces serpentines that extend sinusoidally each in multiple 360° wavelengths in a single turn about the axis of the tube and juxtaposed in plural substantially identical segments disposed with regularity along the axis. Each segment is made to have a length equal to the distance between crests and troughs of the sinusoid, in which adjacent serpentines are joined together at crest and trough, respectively, which makes the serpentines are interconnected 180° out of phase relative to their wavelength.

The process further requires shaping the interconnections between adjacent serpentines which includes providing a notch substantially symmetrically located at either side of the junction of the respective crest and trough. Electro machining of the stent provides serpentines substantially devoid of sharp corners and edges, except at the notches, and gives each serpentine a substantially oval cross-section. The process also interrupts the regularity of the segments of serpentines at least once along the axis of the tube, to provide means for maintaining the length of the tube substantially invariant despite radial expansion of the stent during deployment.

A method of deploying the stent in a vessel or tract in the body according to the invention includes inflating an expansion balloon without a stent to a pressure in a range from about 0.1 to about 0.5 atmosphere to partially inflate the balloon, advancing the partially inflated balloon over a guidewire to the target site, and then retracting the balloon in an uninflated state, so as to ascertain that the passageway to the site will accommodate advancement of a stent crimped on a similar balloon inflated to substantially the same pressure. After the balloon is retracted, a stent is crimped on an expansion balloon substantially identical to the retracted balloon, the balloon is partially inflated sufficiently to distend its proximal and distal ends, as described above, without substantially expanding the stent diameter. Thereafter, the expansion balloon with the stent crimped on it is advanced to the target site, and the stent is deployed.

In a preferred method of the present invention, the openings in the wall of the biocompatible hollow metal open-ended tube are precisely cut by a laser beam, to define the desired sinusoidal pattern of the stent elements. The laser beam is preferably very narrow—about about 35 microns wide or less, is extremely accurate—within tolerances of 2 to 3 microns, and is maintained motionless—except for being switched on and off as cutting is to commence and to cease. In the process, the tube is mounted as a workpiece to allow it to undergo controlled translation and rotation in three-dimensional movement produced by a known apparatus using a processor with computer-aided design (CAD) software. The programmed cuts in the wall with the laser beam not only enables precise definition of the stent pattern, but produces cuts that are virtually burr- and protuberance-free. Care must be exercised to avoid melting the material at the interior surface of the tubular wall, as well as unintended cutting of the opposite side of the tube wall, but these are not difficult safeguards with presently available laser cutting machines. This part of the process produces a relatively smooth stent structure even before special additional machining is employed.

The latter process is electro-machining that automatically concentrates a high current sufficient to attack sharp edges and corners in the tube structure for considerably greater removal of material at those points than elsewhere. This results in a desirable rounding and smoothing of all sharp corners and edges which creates a rounded, preferably oval shaped cross-section of the remaining serpentine ribs of metal that surround the openings. By eliminating sharp edges, corners, and burrs in the stent, there is considerably less likelihood of injury to the vessel wall as the stent is advanced through the vascular system to the target site where it is to be deployed, or as it is deployed, as well as avoidance of damage to and even possible rupture of the membrane of the balloon on which the stent is crimped and deployed.

In that regard, it will be understood that in practice, a guide catheter is inserted initially through the path of the vascular system to be followed by the balloon catheter-mounted stent. The path may be best described as tortuous, with curves, turns, and sharp bends likely to be encountered. Although the guide catheter is in place for most of the passageway, except into the specific designated site, such as a location in the coronary artery, any sharp edges or burrs on the stent could preclude injury-free traversal of this path, by puncturing, cutting, or tearing the guide catheter wall and then the vessel wall itself.

In the electrolytic machining process for edge- and corner-smoothing, the partially completed stent is placed in an electrolytic bath and a voltage placed across the cathode and anode of the apparatus to produce current flow of sufficiently high magnitude to achieve the desired results.

Preferably, the stent itself is used as the anode. The highest current density is present at the edges and corners of the metal in the pattern defined by the openings in the tubular wall, which results in much greater removal of material in those areas than elsewhere in the structure. Up to about five times more metal can be removed at the sharp edges and corners than at more extensive planar surfaces of the structure by appropriately selecting the time, increasingly adjusted current densities, distance between electrodes, electrode diameters, and nature (e.g., constituency) of the electrolyte, so that the edges and corners of the structure are nicely rounded.

If the laser cutting leaves some burrs on the interior surface of the tube wall which are not fully removed because of the cage effect that inhibits electrolytic machining on the inside surface of the tube when electrodes are external to the tube, or if additional rounding of edges at the inside surface is desired, further electro-machining may be performed in which the cathode is a pin that protrudes inside the tube. Periodically, alkaline deposits in the bath arising from the process can be removed by adding acid to enhance the electrolyte, and then conducting further electro machining to produce a shiny, smooth surface throughout the stent.

Animal studies conducted by the applicants herein have clearly demonstrated the importance of rounded elements in the stent, especially the ends and exterior wall surface, to enable easier advancement of the stent through the vessel's tortuous passageway. The arteries are elastic structures that undergo constant contractions and movement, which makes the rounding of even greater importance to avoid injury to this undulating vascular structure.

The basic sinusoidal, sine wave, or sine wave-like pattern of the serpentine elements of the stent are created by the programmed laser cutting of the tube wall. In the preferred embodiment, openings are predetermined to form continuous serpentine ribs lying longitudinally or transversely in the tubular wall. The preferred configuration is one of generally circumferentially oriented serpentines or serpentine elements extending sinusoidally about the axis of the tube in repeating, longitudinally displaced segments along the axis, encompassing the multiplicity of through holes in the wall, and thereby constituting the wall itself. The sinusoidal or sine wave-like pattern of each segment or row of serpentines along the stent axis is composed of multiple 360° wavelengths or cycles of the metallic element in a single turn about the axis, preferably of uniform wavelength. Accordingly, the sinusoidal circumferential patterns are juxtaposed in plural, substantially identical segments disposed with regularity along the axis. Each segment has a length equal to the distance between crests and troughs of the sinusoid, and adjacent serpentines (i.e., adjacent rows of the patterns) are joined together at crest and trough, respectively. Thus, adjacent serpentines are interconnected—periodically joined—at points 180° out of phase relative to their wavelength.

An alternative way of viewing this structure is that if, say, twelve cycles of the sinusoid lie in each segment, the adjacent serpentines are interconnected every 30 degrees (i.e., twelve times) in the full 360° circumference of the tube. The tube is the sole component of the stent, which makes its structure of critical importance to achieving the characteristics of ease of substantially uniform crimping onto a balloon, relatively low force radial expansion, and substantially symmetric opening upon deployment at a preselected site. The serpentines and their interconnections are shaped throughout the length and circumference of the tube wall for optimum achievement of these characteristics, which represent a considerable advance over the prior art. Undesirable events all too often encountered in heretofore available stents, such as twisting of struts that can result in abrasion or cutting of the wall of the blood vessel (or other tract or duct in which the stent is to be deployed) or of the membrane of the expansion balloon, or asymmetric opening of the stent to offer inadequate support of the vessel wall and increased risk of thrombosis, are considerably less likely to occur during deployment of stents of the present invention.

No welds or other special fasteners or questionable joints are present in this stent to interrupt its smooth, continuous structural pattern, which provides the strength and rigidity of tubular construction for desirable full support of the wall of the vessel or tract in which it is deployed, while offering reasonable yieldability for smooth crimping and expansion and flexibility for placement. In the latter respects, the interconnections of adjoining serpentines are preferably characterized by provision of circumferential notches at either side of the junctions between confronting crests and troughs about the juxtaposed segments, and the exterior surface of the wall of the tube is preferably tapered toward its open ends.

The enablement of low force radial expansion of the stent when it is to be deployed is further assisted by subjecting the stent to pre-opening, which pre-stresses or mechanically biases it to eliminate a subsequent need to overcome the inertia of first time expansion during deployment. In this respect, the stent has a first production diameter (i.e., existing at the outcome of the basic manufacturing process), and a second fully deployed diameter (i.e., to which it is radially expanded in the vessel at the target site). The pre-opening of the stent is performed after the basic manufacturing process has been completed, so that the stent as delivered for use has a third diameter intermediate the first and second but still considerably smaller than the second, which enables both ease of crimping and ease of radial expansion.

For example, the initial diameter of the stent lumen may be 1.6 millimeters (mm). Pre-opening of the stent is performed by placing it over a rotating needle so as to increase the lumen diameter to a dimension preferably in the range of from 2.0 to 2.3 mm for vascular uses. A larger pre-opened diameter may be desirable for stent usage in other tracts. This extends the serpentines circumferentially in a uniform manner, causing them to flatten slightly and simultaneously expanding the openings through the wall into a slightly rhombic shape. The pre-opening process thus provides a useful test of the adequacy of likely performance of the device during deployment. If a stent fails to undergo symmetric opening in this partial expansion, it will be deemed unworthy as a production device suitable for implantation, and hence, rejected.

As one of the final steps in the fabrication process, the metal stent is annealed to provide it with additional radial strength without adversely affecting the longitudinal flexibility of the structure. The annealing step is preferably conducted after the pre-opening of the stent but may alternatively be performed beforehand.

The stent characteristics of ease of full and symmetric expansion remain despite an initial crimping of the stent onto the expansion balloon, either by the physician at the time the stent is being implanted, or by the manufacturer if a pre-assembly of the stent on the balloon is to be supplied for use. This highlights a further advantage of pre-opening the stent—namely, that the balloon is more easily inserted into the stent than would have been the case had the stent been left with its original diameter (basically, that of the starting tube). Also, if the serpentine structure is annealed in the pre-opened condition, the metal tends to be relaxed in that state. Before the crimping, the balloon is put under vacuum to assure a more complete securing of the stent on the balloon. Afterward, the balloon is partly inflated to stabilize the location of the stent intermediate the ends thereof as mounted on the balloon.

The importance of a symmetric opening of the stent as it is being deployed at the target site cannot be overemphasized. With a stent according to the present invention, symmetric expansion is achieved with even low pressure balloons, at pressures in the range of from 6 to 8 atmospheres. A single balloon can therefore suffice for mounting of the stent, advancing it to the target site, and deploying it. The primarily longitudinal, flattened oval-like openings defined by the circumferential serpentine elements of the stent are readily shifted during deployment to a rhombic or net-ike shape. Symmetric opening gives much greater likelihood of a successful vascular stent deployment without injury to the vessel, with stabilization of the vessel wall, and with greater probability of avoiding restenosis. Results of corresponding importance are achieved with endoluminal stents for use in other tracts of the body.

To provide the tapering of the outer diameter of the tube toward its open ends, the tube is polished in a smooth progression from its mid-section. This gives it improved flexibility at the ends and greater compliance with the wall of the vessel at the implant site. The uniform diameter of the tube's axial lumen is substantially unchanged throughout its length by this process, so as to avoid impeding or creating turbulence in the blood flow that might otherwise cause thrombus formations.

The stent of the present invention is adapted to automatically compensate for a reduction in its length otherwise occasioned during deployment by radial expansion. In essence, the stent is provided with means for maintaining its length invariant despite the opening of its diameter. The preferred means for performing this function comprises serpentine elements structured to undergo a change in length in a direction opposite that caused by the partial flattening of the circumferential serpentines with the increased diameter of the stent. Alternative means could include, for example, the use of selected thinner-walled regions to facilitate unequal movement of members for length compensation purposes. While no particular difficulty is encountered to fashion elements of different thicknesses a the same time that other features of the stent design are constructed, by use of a 3-D workpiece and Cad-controlled laser system, in the preferred embodiment serpentine elements are provided in the tubular wall in transverse orientation relative to that of, and in at least one location intermediate, the circumferentially running serpentines, as the compensating means. The transverse serpentines are connected to selected points of the most closely adjacent circumferential serpentines and are also of sinusoidal pattern, but run longitudinally and are separated from one another at predetermined points about the circumference of the tube. The selected separations avoid imposing constraints on the diameter of the stent at the location of the transverse elements during expansion of the stent, but do not substantially affect the rigidity of the stent. During crimping of a stent with such length-compensating means onto a balloon, additional care is required for uniform crimping of unconnected portions of the compensating sections.

The stent's automatic maintenance of substantially its original length during deployment makes it unnecessary for the physician to pre-calculate or otherwise determine changes in length of the stent to assess adequacy of coverage of the affected tissue at the target site in the vessel. Additionally, the length-compensation feature lessens the likelihood that two stents must be implanted end-to-end where, but for a change in length, a single stent of standard length would suffice.

Further distinctions of the present stent from prior art stents include the following. Comparing the preferred embodiment with wire stents, the width of the support structure elements—here, the serpentines—is about 140 microns, with twelve full wavelengths or cycles in each row about the circumference of the tube. Hence, the total area of support afforded by the present stent is much greater than that provided by a wire stent with its typical four or five wire segments about the periphery. Further, the support offered involves more than simply the width of the wall elements. For example, if each serpentine has a width of 140 microns and a thickness of 70 microns, the width to thickness ratio is a factor of 2:1, with achievement of full mechanical strength. The diameter of the wire in a typical wire stent of the type referred to above is in a range from about 150 to 180 microns. The coronary arteries have diameters as small as 2.0, 2.5, or 3 mm. The tubular wall thickness (and therefore, the individual element thickness) of the present stent can be significantly increased without loss of its lumen size advantage over the wire stent. For example, the difference between the wire diameter (doubled, as the thickness occupies "both sides"—actually the entire surface of the vessel wall, when viewed in a cross-section through the vessel's lumen) and the serpentine's thickness (also doubled) is about 200 microns (or 0.2 mm), which may range from about 6% to about 10% of the total diameter of the vessel. The stent of the present invention thus offer a substantial advantage in size of passageway for blood flow over that available with the typical wire stent, and would continue to do so with increase in wall thickness of up to 100 microns.

Compared to tube-type stents currently in common use, the present stent does not use a system of parallel longitudinal struts and connecting bridges—instead, using serpentines of sinusoidal pattern running circumferentially—nor have rectangular openings in the tube wall as with the prior stents, instead producing a rhombic, net-like structure. Rather than having elongate members joined by distinct bars or bridges, the present stent's serpentines enjoy periodic smooth interconnection in an integrated structure, with circumferential notches to facilitate both crimping and radial expansion. Cross-sections are rounded, preferably oval-shaped, rather than sharp. Additionally, because the present stent is provided for use in a pre-opened condition or state, and no intersecting elongate members as such are present, a slightly spring-like reaction occurs when the stent is crimped, but the stent undergoes smooth and symmetric expansion with no undesirable elastic recovery during deployment. At points of interconnection between adjacent serpentines, considerable pressure may be exerted to firmly crimp the stent on the balloon without concern for the sharp edges often found in prior art stents that might cut into the balloon's membrane.

In preparation for implantation, the stent is crimped on and intermediate the ends of a deflated expansion balloon, and the balloon is then inflated to a pressure of from about 0.2 to about 0.4 atmospheres, sufficient to distend its end portions that extend beyond the respective ends of the stent without substantially expanding the crimped stent thereon. This technique of firmly attaching the stent on the balloon serves several purposes. First, any slipping or dislocation of the stent relative to its initial crimping site is avoided both before and during advancement to the target site in the vessel or tract. Firm retention is important here because the stent is not very visible during the procedure, reliance being placed instead on the position of a radiopaque marker dot on the balloon which is visible by X-ray and identifies the original relative location of the stent. Inaccurate placement of the stent for deployment will occur, however, if the stent slipped along the balloon during the journey to the target site, with resultant failure to cover the full site of the injured tissue, leading to a need to implant a second stent or leaving a prime site for restenosis.

Second, the slightly inflated end portion of the balloon ahead of the crimped stent prevents the stent from cutting into arteriosclerotic vessel portions as the stent is advanced to its target site. Third, if an inability to advance the stent to its final destination is encountered, such as because of very sharp bending of the arteries, the stent can be retracted into the guiding catheter, protected by the other slightly inflated end portion of the balloon, without substantial risk that the stent will be stripped from the balloon and left in the vascular system, possibly leading to infarction.

In a preferred test run, an expansion balloon without stent is partially inflated to a predetermined pressure such as the 0.2 to 0.4 atmosphere range, is then advanced over a guidewire to the target site, and then depressurized and withdrawn in the uninflated state from the site and from the vascular system. If the path is found by this method to be open and unimpeded, the procedure may be repeated with a stent on a substantially identical balloon inflated to a substantially identical pressure with greater assurance of its success.

BRIEF DESCRIPTION OF THE DRAWINGS

The above and still further aims, objects, features, aspects and attendant advantages of the present invention will become apparent from the following detailed description of a preferred embodiment and process of manufacture thereof constituting the best mode presently contemplated of practicing the invention, when taken in conjunction with the accompanying drawings, in which:

FIG. 1A is a perspective view primarily from the side.

DETAILED DESCRIPTION OF THE PRESENTLY-PREFERRED EMBODIMENT AND METHOD

Before commencing the detailed description, several comments should be made regarding the Figures of drawing. The drawings are not intended to be to scale. Where appropriate, the representations are simplified, such as in FIG. 1A, the omission of the other side of the stent which could obviously be seen in this view but would unnecessarily clutter and obscure the portion of interest, and in FIG. 2A, the detail supplied in only a part of the stent although it will be understood that the same pattern would be present throughout. In some instances, the Figure or a portion thereof is exaggerated for emphasis.

Figure 1A:
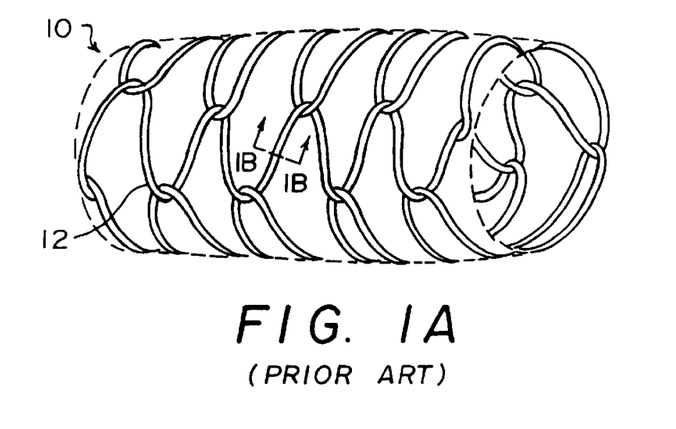
Figure 1B:
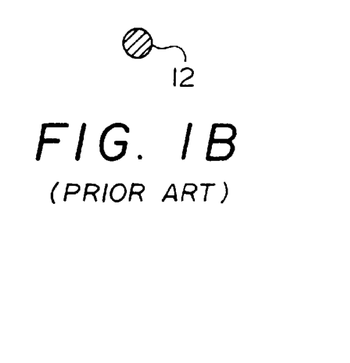
FIG. 1B is a cross-section of an individual wire, of a wire-type stent of the prior art.

Referring to FIG. 1, a prior art wire stent 10 is illustrated in side view in part A of the Figure, and the round cross-section through an individual wire 12 of the stent is shown in part B. The wires 12 are interconnected in a zig-zag pattern similar to that of a chain-link mesh used for fences. The wire diameter is large but despite this, there is only what amounts to line contact between the individual wires and the tissue of the vessel wall when the stent is fully deployed. Some of the disadvantages of wire-type stents have been described above.

Figure 2A:
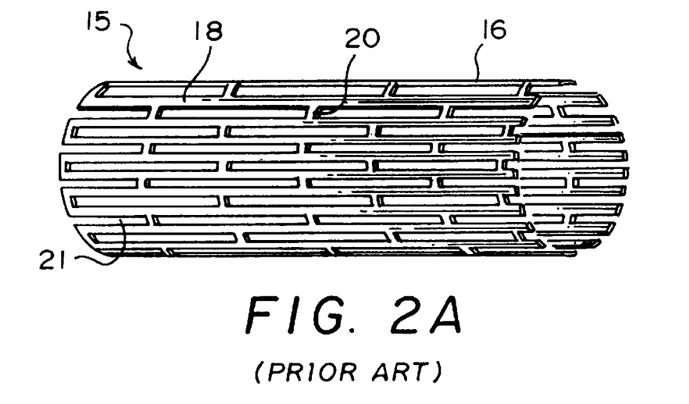
FIG. 2A is a partial perspective view, primarily from the side, of a prior art tube-type stent.
Figure 2B:
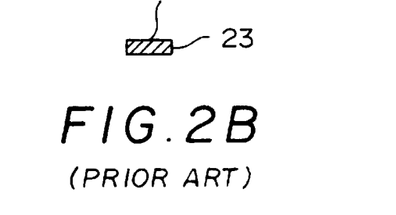
FIG. 2B is a cross-section of an individual strut thereof.

In FIG. 2, part A, a tube-type stent 15 is fabricated from tubing 16. A plurality of parallel, longitudinally oriented struts 18 (in the unopened state) interconnected by bars or bridges 20 at intersections of the struts define a multiplicity of through-holes 21 in the wall of the tube. Greater detail may be seen in the fragmentary portion of FIG. 3, although there the part is in the opened state. Part B of FIG. 2 illustrates the rectangular cross-section through a strut 18. Here, also, the drawbacks of this currently highly popular type of stent have been discussed above.

Figure 3:
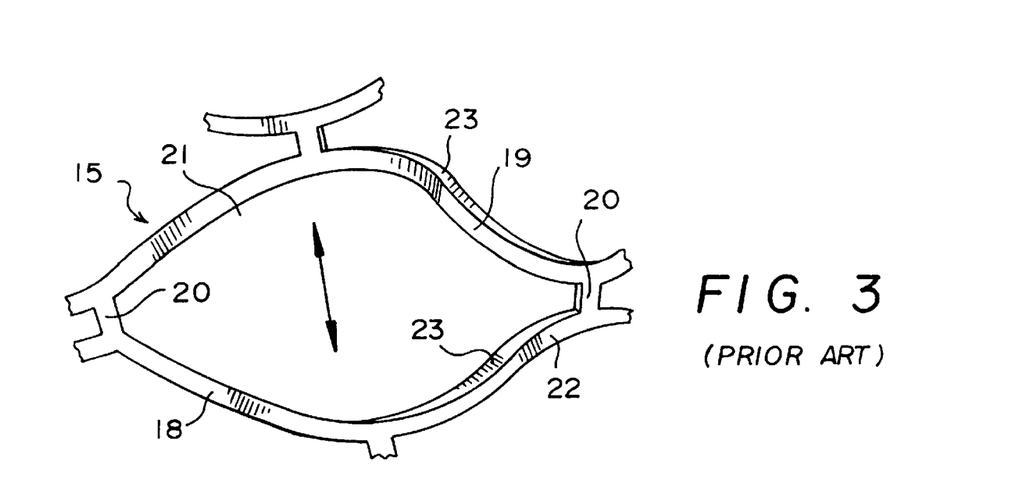
FIG. 3 is a fragmentary perspective view of a portion of the prior art tube-type stent of FIG. 2A, during expansion for deployment in a vessel.

However, one of the more critical aspects of the stent of FIG. 2, namely, its ability or inability to open symmetrically during deployment, is graphically illustrated in the fragmentary diagram of FIG. 3. Common elements in these and others of the Figures are represented by common reference numbers. As shown in FIG. 3, stent 15 is in process of being deployed. As a consequence of structural deficiencies of the stent of this example, upon expansion of the diameter of the stent under pressure exerted on its interior surface by inflation of an expansion balloon (not shown) on which the stent is mounted, at least the initial parts of two of the struts 18, namely 19 and 22 in this example, have undergone twisting or torquing. This deformation has exposed virtually the entire length of the thin edge 23 of each of struts 19 and 22 so as to actually or potentially contact either the interior surface of the wall of the vessel in which the stent is being deployed or the external surface of the membrane of the expansion balloon. This twisting occurs at initial expansion of the stent at pressures between 2 and 4 atmospheres.

Figure 4A:
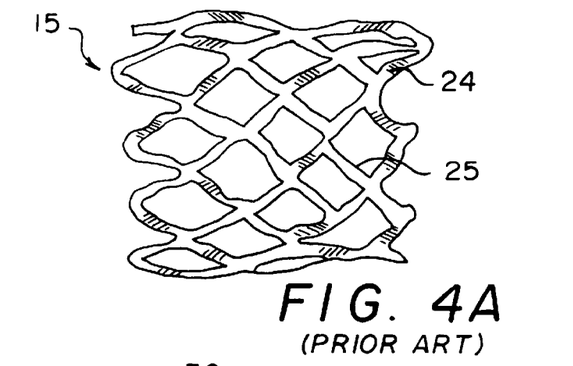
FIG. 4A is a perspective view of the prior art tube-type stent of FIG. 2A in its expanded state.
Figure 4B:
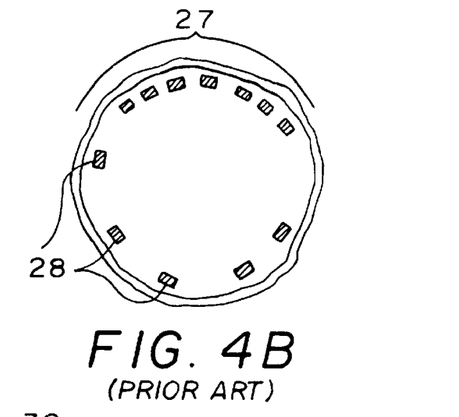
FIG. 4B is a cross-section view through a vessel with that opened stent.

If a few of the struts, such as only two to four of the struts undergo twisting, the remaining struts will stay in a primarily parallel configuration. That is, some of the struts are extended from their initial positions, while others have yet to open. The struts that have yielded will tend to continue to do so, which in turn tends to keep the others unopened. Further increase in balloon size and pressure will open the already deformed and twisted segments even more, resulting in a considerable and dramatic unequal and non-uniform opening of the individual stent struts, graphically illustrated in FIGS. 4A and 4B. The stent 15 (FIG. 4A) is misshapen as some of the struts such as 24 have undergone little movement or extension, while others such as 25 have therefore been caused to overextend and twist in the manner shown in FIG. 3. In FIG. 4B, the cross-section through the wall of the vessel in which the stent is deployed or being deployed reveals that a cluster 27 of the struts remain substantially unopened, while the other struts are primarily overextended. The holes 21 in the stent will therefore also have assumed various non-uniform shapes and sizes as a result of the asymmetric expansion While it is certainly possible that this stent as deployed may not cut or abrade tissue or puncture the expansion balloon, it appears to be destined to produce deformation of the vessel wall, and to create turbulence in the blood flow through its region of the vessel which can produce thrombus formation.

Figures 5A, 5B, 5C:
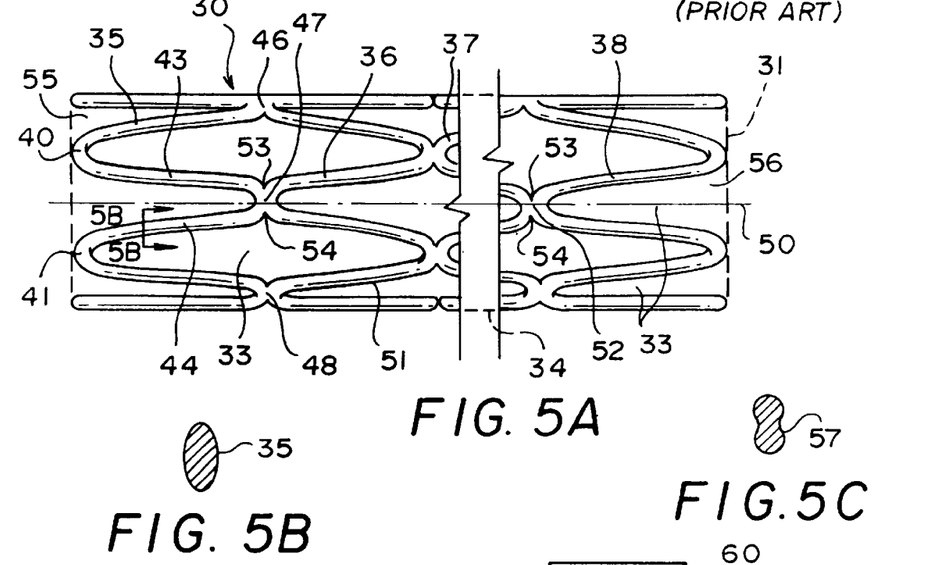
FIG. 5A is a side view of a vascular or endoluminal stent according to the present invention, in a pre-opened state for use.
FIGS. 5B and 5C are cross-sections through a serpentine illustrating preferred and alternative shapes.

Referring now to FIG. 5A, a stent 30 designed and fabricated according to the present invention, is shown in a pre-opened state as it would be supplied in volume to hospitals, medical centers, clinics, and other appropriate facilities for implantations by physicians. Stent 30 is constructed from a hollow biocompatible metallic tubular structure or member 31 (shown in phantom). The tubular member is provided with a multiplicity of openings 33 through its wall 34 which define the stent configuration. The openings 33 are precisely cut, for example, within a tolerance of 2 to 3 microns, by a narrow laser beam, on the order of 35 microns or less.

According to the invention, the biocompatible hollow open-ended tube 31 is the sole member from which the entire stent is fabricated, and the configuration defined by the multiplicity of openings 33 through the wall comprises a plurality of serpentine elements 35, 36, 37, 38, and so forth, in the wall that run circumferentially in juxtaposed substantially sine wave-like or sinusoidal patterns. All patterns are of a uniform number of multiple cycles—six in this exemplary embodiment (i.e., one cycle constitutes a full wavelength or 360° of the sinusoid—for example, from the crest 40 to the adjacent crest 41 in serpentine 35, but there are effectively two portions, e.g., 43 and 44 in each wavelength). A 360° wavelength of the sine wave is not to be confused with the 360° circumference of the stent tube. Adjacent ones of the serpentines, such as 35 and 36, are offset from one another by a predetermined phase difference at periodic interconnecting points such as 46, 47, and 48 between them about the circumference of the tubular wall 34. The patterns are uniformly displaced in juxtaposed segments or rows longitudinally along the axis 50 of the tube, and these segments may be viewed as occupying a length of the tube substantially equal to the distance between the crest and the trough of the respective serpentine, such as from 40 to 47 in the case of serpentine 35.

The phase difference at interconnecting points such as 48 between adjacent longitudinally-displaced sine wave-like patterns of the serpentine elements, such as 35 and 36, is 180°, viewed as the offset between cyclical waves of the two. This phase difference may alternatively be viewed as being less than 180° relative to the 360° circumference of the tube and the number of sine wave-like cycles in each of the circumferential patterns, such as 30° for the number of cycles of the sinusoidal pattern in the exemplary embodiment of FIG. 5A.

Each of the interconnecting points, such as 52 between serpentines 37 and 38, includes means in the form of circumferential notches such as 53 and 54 at either side of the respective interconnection to enhance crimping and symmetric expansion of the stent on a balloon, or means otherwise adapted to exert relatively uniform radial outwardly-directed forces from within the tube. Each of the serpentine elements has a rounded cross-section, preferably an oval cross-section as shown in FIG. 5B for serpentine 35.

Preferably, the flattened, closed, substantially oval-shaped openings 33 are sized in a range of ratios of length to width of from 4:1 to 10:1. The length of each opening 33 is typically in a range from about 2.0 to about 4.0 mm, and the width in a range from about 200 to about 300 microns. The width of each serpentine rib 38 is preferably from about 120 to about 240 microns, and the thickness in a range from about 65 to about 100 microns depending on the specific point of along the length of the stent at which the measurement is taken, if the thickness of the tube wall is varied from middle to each end to taper the outer diameter of the stent toward the ends.

Each end 55, 56 of the tube 31 is a series of undulations in the sine wave-like pattern of the serpentine occupying that respective segment in the basic stent structure of the invention.

Although an oval cross-section of the serpentines (shown in FIG. 5B) is preferred, produced in part as a result of electro machining to be described below, the serpentines may have a different rounded cross-section if desired. For example, they may be shaped by the laser cutting and subsequent electro machining to be similar to an erythrocyte or a bone, rounded but with narrower mid-section and thicker ends, as shown at 57 in FIG. 5C. Laser machining processes can also be used not only to cut out the shapes of the openings but also to narrow the mid-portion of the width of each rib in that manner. Such shapes enhance the flexibility and thereby ease of advancement and extension of the stent within the vessel, without adversely affecting the dimensional stability of the stent that assures its ability to withstand compression in response to recoil of the vessel wall.

Figure 6:
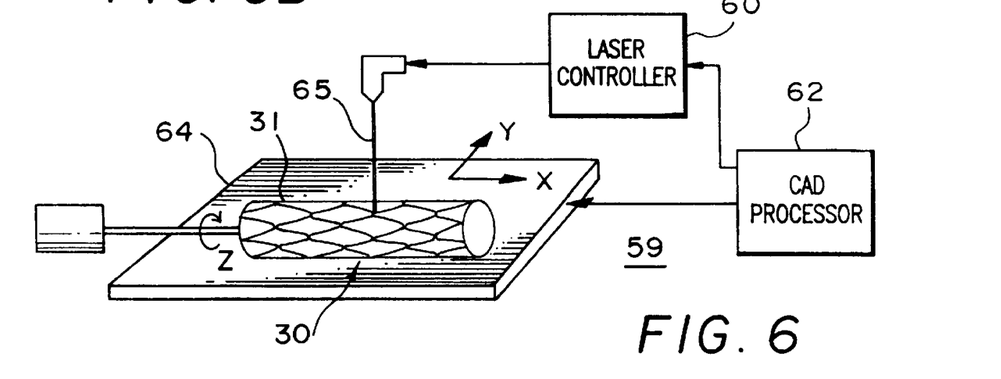
FIG. 6 is a diagram partly in block form and partly in schematic representation form, of apparatus for performing the laser cutting portion of the stent fabrication process of the invention.

As shown in FIG. 6, the apparatus 59 for producing the openings 33 and the serpentines such as 35 associated with them in stent 30 includes a laser 60 controlled by a CAD processor 62, and a worktable 64 adapted to produce 3-dimensional movement of a workpiece along or about at least three distinct axes, X, Y, and Z. In particular, the laser is oriented to direct a laser beam 65 upon a workpiece for program-controlled cutting and machining thereof. Here, the workpiece is moved along or about the axes, and the laser beam is held fixed on the space occupied by the workpiece—except for being switched on and off as cutting is to commence and to cease.

In this process, the tube 31 which is the starting material for stent 30 is mounted as the workpiece in apparatus 59 to allow it to undergo controlled translation and rotation in three-dimensional movement. The movements of tube 31 are controlled by a program developed to achieve the serpentine patterns of the stent 30, while the laser beam 65 is switched on and off as necessary to produce the programmed precision cuts in the wall 34 of the tube. All cuts are made within time intervals and tolerances necessary to complete the cutting of the openings 33, including the partial openings at both ends 55, 56 of the tube, and thereby the cutting of the serpentine patterns, substantially free of burrs and protuberances. The resulting partially completed stent 30 is a relatively smooth structure as a result of its process of fabrication, but according to the invention, further machining is performed to eliminate all sharp edges and corners of the structure.

To that end, the partially completed stent is subjected to electro machining by an electrolytic process, such as that available through AVT Corporation of Germany. Alternatively, similar results may be possible with electrical discharge machining. In the electrolytic process, the partially completed stent is immersed in an electrolyte bath as the anode, and a voltage is applied across the stent and the cathode to produce a high current density—up to several hundred amps at a mean rate of 15 seconds for the internal and external surfaces of the tube—through the electrolyte. The heaviest concentration of current density is at the discontinuities of the stent structure, i.e., sharp edges, sharp corners, burrs, projections, and the like, which removes metal at those points and regions at about five times the removal rate for large planar regions.

Both internal and external surfaces of the tube wall are subjected to the high current, the latter by inserting the cathode into the axial lumen of the tube as the anode. The electrolyte is of known type that will not boil while supporting current densities necessary to produce uniform rounding of the stent structure. As a consequence of this action, the stent structure is rounded and smoothed at all of its corners and edges. Further, by replenishing acid in the electrolyte depleted by the processing, followed by additional electro machining, a shiny, smooth surface is provided over the entire stent structure.

At this point in the processing, the stent 30 is composed of a plurality of continuous serpentines juxtaposed along the tube in circumferentially extending sinusoidal patterns that surrounding respective groups of the openings 33 in a completely smooth, rounded metal structure, essentially as shown in FIG. 5A. However, FIG. 5A is also intended to illustrate the pre-opened characteristic which is an important part of the stent fabrication process. The circumferential notches 53, 54 at confronting midpoints of the interconnections such as 52 (FIG. 5A) of respective crests and troughs of the adjacent serpentines are of special importance for an equal and symmetric opening of the stent and also to allow a firm crimping of the stent onto the uninflated balloon. To that end, the notches my be protected from subjection to the electro machining process to prevent them from being overly smoothed, or may be recut after that portion of the process.

On completion of the electro machining portion of the stent fabrication process, the stent is opened to a limited extent to eliminate the inertia that prevails with a first-time expansion of the stent. This partial expansion, termed the "pre-opening" of the stent herein, is effective to relieve stresses or to pre-stress the overall structure. In effect, the tube is mechanically biased to substantially reduce the forces needed to overcome inertia and to enable substantially symmetrical expansion of the stent during its deployment. If the initial outer diameter of the lumen of the stent is 1.6 mm, which in any event should correspond to the outer diameter of the starting tubular material, the pre-opening expansion process may consist substantially of positioning the stent on a rotating needle (not shown) which operates to increase the lumen diameter so that the outer diameter of the pre-opened stent may be at any of a continuum of predetermined dimensions up to that corresponding to the largest diameter available using the rotating needle. Preferably, for a starting diameter of 1.6 mm, the pre-opened diameter is at the lower end of the range from 2.0 to 2.3 mm. In any event, the pre-opening should result in an inner diameter of the stent which allows the stent to slide comfortably over the uninflated balloon, and then to crimp the stent onto the balloon.

The annealing of the stent at this point in the overall stent fabrication process is performed by heating the serpentine structure to a temperature that depends on the material from which the original tube was produced, for a predetermined interval of time. Suitable materials include medical grade stainless steel, such as 316L stainless steel, tantalum, titanium, platinum, and iridium. Even a suitable polymer of appropriate physical, mechanical and X-ray characteristics may be used, subject to the availability of a substitute process analogous to electro machining—which would not work for a non-metal—to round the corners and sharp edges of the partially processed stent The pre-opened stent is depicted in the structure of FIG. 5, and this form as annealed is the preferred form of device delivered for implantation by the physician, except for the inclusion of length compensating means to be described presently.

Figures 7, 8, 9:
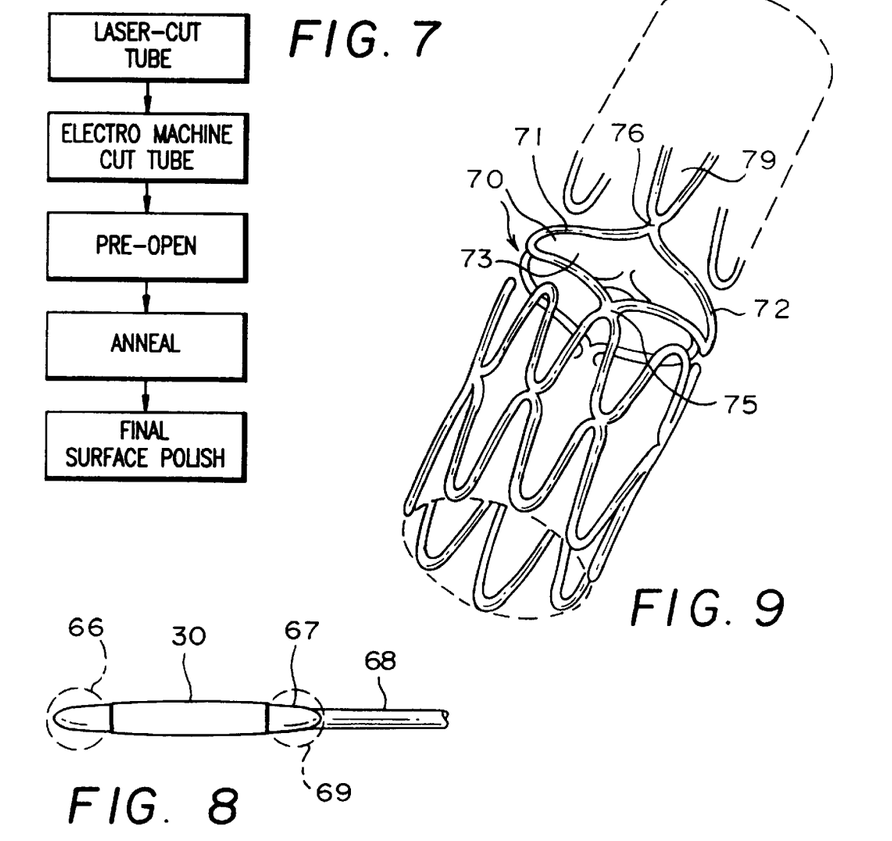
FIG. 7 is a flow chart of the basic stent fabrication process of the invention, exclusive of the pre-opening of the stent.
FIG. 8 is a side view of a stent mounted on a balloon, with an exaggerated phantom portion illustrating the technique of the invention of partial inflation of the balloon to expand its ends for retention and delivery of the stent for deployment.
FIG. 9 is a perspective view of a stent illustrating incorporation of length-compensating means into the stent structure.

The fabrication process employed to produce the basic stent as described thus far, is illustrated in the flow chart of FIG. 7, which requires no further explanation.

Alternatively, the completed stent 30 may be pre-mounted on a balloon 67 of a catheter body 68, as shown in FIG. 8, and delivered in a sterile package as a complete assembly ready for use by the physician. The principal advantage of such an assembly is that it eliminates the need for skill in crimping the stent onto the balloon, which requires sufficient experience to avoid damage to the balloon by an overly tight crimp, or the possible separation of the stent or injury to the vessel wall by an overly loose stent. The pre-mounted device need simply be unpackaged and used to implant the stent. However, each patient differs from the next insofar as vessel diameter and condition are concerned, which may necessitate the use of different balloons despite the possibility that the same type of stent could be employed in each case. Indeed, twenty different types of balloons, for example, might be usable with a single type of stent. The availability of an expansion balloon of particular dimensions and characteristics with a stent also of particular dimensions and characteristics each time a procedure is to be performed could require a considerable inventory of different pre-mounted stent/balloon assemblies.

Moreover, it may happen that the same type of balloon—of medium compliance —can be accommodated by a vessel of 2.5 mm or one of 3.2 mm, simply by inflating to higher pressure. Also, some balloons are more amenable to advancement or retraction through sharp bends in the vessel lumen but do not tolerate high pressures, while other balloons have greater stiffness and ability to withstand higher pressures. Therefore, to customize the therapeutic decision on an individual basis, it is preferable for the physician to have available stents which can be selected individually and mounted on a desired type of balloon, also selected individually, based on the physician's familiarity with each and desire to provide the optimum results for a particular patient and vascular structure and condition. Consideration of balloon characteristics including size, construction, membrane material and other properties, and other specific patient factors including implant target site, vessel sizes, length of the tissue region to be treated, and so forth, will be part of the selection process.

Whether supplied unmounted, or pre-mounted on a balloon, the stent after crimping onto the selected balloon should have an outer diameter ranging from about 0.9 to about 1.2 mm. When filly deployed in the vessel at the target site by inflation of the expansion balloon, its outer diameter will typically lie in a range from about 2.5 to about 5.0 mm, with a maximum of about 6.0 mm. Final deployed diameter, of course, must be adequate to assure retention of the stent in the vessel in firm contact with the vessel wall (and, if desired, even partly imbedded in the vessel wall to present a relatively smooth continuous lumen to lessen the possibility of blood flow turbulence).

The dimensions of the serpentines and of the openings between them in the tubular wall of the stent, as well as the characteristics of the balloon, will ultimately determine the minimum diameter to which the stent may be crimped on the balloon—typically, 1.0 mm—and the maximum diameter to which the stent may be dilated by the balloon during deployment—typically, 6.0 mm (inner diameter).

The stent may be produced in lengths ranging from about 5.0 to about 25.0 mm. But stents of the various prior art types are typically supplied in two standard lengths, one of which is toward the lower end of the range (e.g., a length of about 8.0 to about 9.5 mm) and the other in the mid to higher end (e.g., a length of about 15.0 mm), because the expansion balloons for deploying the stents are customarily available in a length of either about 10 mm or about 20 mm. Other stent lengths are available on a custom basis, but occasionally it is necessary to implant two stents actually or virtually abutting each other when the length of the injured tissue at the target site is greater than accommodated by a single available length, or because the stent length is limited by a need for sufficient flexibility to be advanced through the vascular system to the target site.

Referring again to FIG. 8, for purposes of implanting the stent according to the invention, the stent 30 is crimped on expansion balloon 67 with the balloon under vacuum, and then the balloon is initially inflated to a pressure of from about 0.1 to about 0.5—nominally, 0.2—atmospheres. The specific pressure selected should be sufficient to partially inflate and distend the balloon at its distal and proximal ends which extend beyond the respective ends of the stent (by proper selection of stent and the balloon lengths) as illustrated by exaggerated bulbous or distended ends 66 and 69 of the balloon shown in phantom, but insufficient to expand the diameter of the stent as crimped on the balloon. With this slight inflation at its ends, the balloon provides a desirable cushion to protect the stent, to prevent it from being dislodged, and to keep it from scraping the vessel wall during advancement to the target site, by retaining it firmly centered along the balloon's length, as well as for other purposes mentioned earlier herein.

In practice, a slightly inflated balloon (to about 0.2 atmospheres pressure)—without stent—is advanced over the guidewire to the target site in the vessel where the stent is to be deployed. This "dummy" balloon is then depressurized and retracted from the vascular system and from the guide catheter. The purpose of this exercise is to ascertain that the target site is accessible through this path with a partially inflated balloon. If the access is achieved, the physician knows that a stent crimped on the balloon, which is then partially inflated as described above, can also be advanced to the target site. In part, this is assured because, given the same inflation pressure, a balloon without stent has a larger diameter than when it carries a crimped stent.

The proper inflation pressure for the balloon for this purpose depends to a great extent on the composition and characteristics of the balloon membrane—for example, whether it is polyurethane, polyimide, or some other material, whether it is highly flexible or somewhat stiff, and its length. Also, the physician should visually inspect the assembly of the stent crimped on the balloon before it is inserted and advanced in the vessel, to determine how it behaves with the lowest pressure deemed suitable for stent retention. If the pressure gauge is inaccurate at the low pressures of from 0.1 to 0.5 atmosphere, the physician must determine the "right" pressure empirically, by look and feel, which requires some experience in using and implanting stents.

Another advantage of partial inflation of the balloon for delivery of the stent is that the mounted stent is readily withdrawn if problems—such as sharp bends in the vascular path—are encountered during attempted advancement. In contrast, if the stent is being retracted while crimped on an uninflated balloon, extreme care is required to assure that the stent will not be dislodged while moving through the coronary artery are any other curved portion of the path through the vascular system, or when retracting the balloon and the stent into the guiding catheter. The edge of the stent may, for example, hook into the opening at the distal end of the guiding catheter. But if the stent is retained at approximately the middle of the partially inflated balloon, it is more easily withdrawn without incident. This rescue maneuver is crucial to prevent the loss of an unopened stent, especially in a coronary artery; otherwise, the patient's hemodynamic condition could deteriorate rapidly and death could ensue during the procedure.

As a stent is deployed by steadily increasing the inflation pressure to the expansion balloon, the diameter of the stent will slowly increase with expansion of its lumen. This causes a reduction in the length of the stent, which ordinarily occurs with any stent design and which must be factored in to determine in advance whether sufficient coverage of injured tissue at he target site will be achieved using a single stent. According to the present invention, means are provided by which the stent undergoes an automatic controlled extension of its length to compensate for the shortening of its length that would ordinarily occur when its lumen diameter is expanded.

This is achieved by incorporating into the stent, elements which undergo a change that leads to a measured increase in the opposite direction. In the preferred embodiment, shown in FIG. 9, the uniform longitudinal displacement of the circumferential sine wave-like patterns is interrupted at least once along the stent's axis by transversely oriented serpentine elements 70 that run longitudinally within the tube wall in juxtaposed at least partial sine wave-like patterns such as 71, 72, and that serve to shape openings such as 73 through the wall between them. Adjacent transverse patterns are offset from each other by a 180° cyclical phase difference at interconnecting points between them along the tube's axis, using the same analysis as was applied in the case of the circumferentially extending serpentines of FIG. 5A. These transversely oriented serpentine elements are adapted to maintain the length of the tube substantially invariant with radial expansion of the stent. To that end, they are connected to adjacent points of the circumferential serpentines, as at 75 and 76, but unconnected at their own crests (or troughs) so as not to constrain the diameter of the stent at those points.

Figures 10, 11:
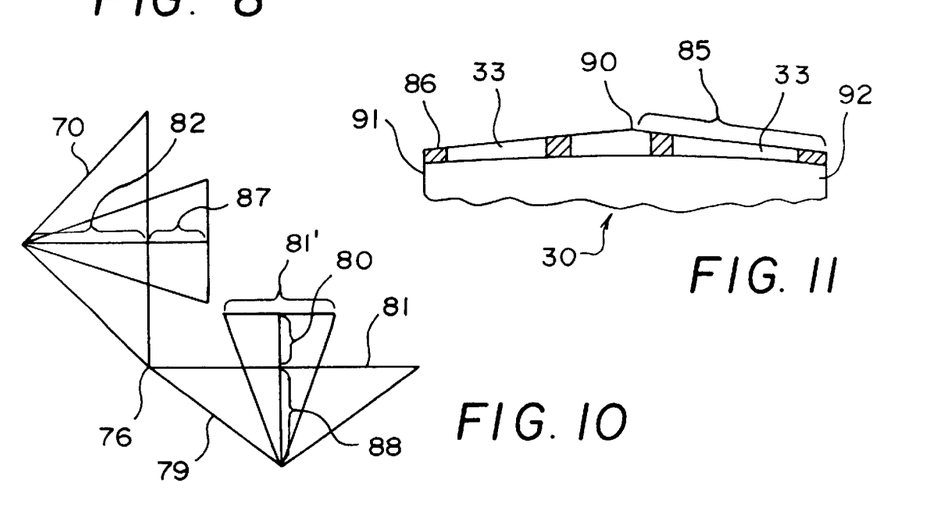
FIG. 10 is a diagrammatic representation of length extension versus length contraction in the structure, to illustrate compensation performed by the structure of FIG. 9.
FIG. 11 is a fragmentary side view of the stent of FIG. 5, illustrating the taper in the outer diameter of the stent from the mid-section thereof toward either end.

This length-compensating effect may be seen by reference to analogous triangles of the diagrammatic representation in FIG. 10, which may be used as a mathematical model for calculation. Triangles 70, 79 represents related ones of the transverse and circumferential serpentines of FIG. 9, connected at point 76. As the short segment 88 of triangle 79 is extended (by a length 80, consistent with the stent being expanded in deployment), so is the short segment 82 of triangle 70 (by a length 87). The dimensions of the transverse serpentines relative to the cirumferential serpentines should be set such that length extension 87 matches the contraction of the length of segment 81 (corresponding to the long axis of circumferential serpentine 79) to new length 81'.

At a desired point in the fabrication of the stent of the invention, preferably after the openings 33 have been cut to form the serpentine structure and the electro machining has been performed, the stent may be polished to provide it with a taper 85 (FIG. 11) of its outer diameter 86 by removing sufficient material from the outside surface of the tube wall progressively from its mid-section 90 to each end 91, 92. For example, the taper may be sufficiently pronounced to make the wall thickness 65 microns at each end, and a larger dimension in a range from 75 to 90 microns at the mid-section of the stent, with smoothly varying wall thickness. No change or only a small change is made in the inner diameter of the stent so that the lumen is unaffected. This longitudinal variation in outer diameter of the stent allows the stent to adapt itself to proper compliance with the vessel wall, with greater flexibility at the ends, without relinquishing the rigidity afforded through the mid-section of a tubular wall. As a result, bending stresses that would otherwise occur at the ends of the stent on the vessel wall, and which could produce restenosis, are considerably reduced. Preferably, the outer diameter of the stent at the ends is about 80–95% of the outer diameter at its mid-point.

Although a presently preferred embodiment and methods of the invention have been shown and described, it will be apparent to those skilled in the art from a consideration of the foregoing detailed description, that variations and modifications of the described embodiments and methods may be made without departing from the true spirit and scope of the invention. It is therefore desired that the invention be limited only by the following claims and the rules and principles of applicable law.

What is claimed is:

1. A method of facilitating delivery of a vascular or endoluminal stent to a preselected site in a vessel of a patient where the stent is to be deployed to maintain the lumen of the vessel open, said method comprising the steps of:

selecting a balloon catheter having a balloon with a length greater than the length of a stent crimped thereon so that the ends of the balloon project beyond the ends of the stent; and partially inflating the balloon to distend the exposed ends thereof without materially expanding the diameter of the stent before advancing the stent-mounted balloon catheter through the vessel, to maintain the stent in place on the balloon and to provide a cushion for protecting the wall of the vessel during delivery of the stent to said preselected site.

2. The method of claim 1, wherein the step of partially inflating the balloon comprises inflating the balloon to a pressure in a range from 0.1 to 0.5 atmosphere.

3. The method of claim 1, including selecting said balloon catheter with a stent which was pre-opened to a diameter intermediate its production diameter and its fully deployed diameter before being crimped on the balloon, to verify symmetrical expansion of the stent and to lessen the balloon inflation pressure necessary to fully deploy the stent.

4. The method of claim 1, including selecting said balloon catheter with a stent fabricated from a single tube open-ended metal tube having a multiplicity of holes in a symmetrical pattern through the tube wall defining a plurality of struts bounding said holes in longitudinally repeating serpentine patterns with notches at intersections of the struts, to enhance longitudinal flexibility, radial rigidity and symmetrical expansion of the stent.

5. The method of claim 1, including selecting said balloon catheter with a tubular stent having a multiplicity of holes in a symmetrical pattern through the tube wall defining a plurality of struts bounding said holes, in which said struts have one of an oval or erythrocyte cross-sectional shape.

6. The method of claim 1, including first advancing an identical slightly inflated balloon catheter ithout a stent mounted thereon through the vessel to said preselected site as a prior indication of accessibility of the stent-mounted balloon catheter to said preselected site.

7. A method of producing a stent delivery system for delivering a vascular or endolurninal stent to a preselected site in a vessel or tract of a patient at which the stent is to be deployed to maintain the lumen of the vessel or tract open, comprising the steps of:

selecting a metallic stent for mounting on a balloon catheter;

pre-opening the stent to a diameter intermediate its production diameter and its fully deployed diameter; and crimping the pre-opened stent snugly onto the balloon of the balloon catheter.

8. The method of claim 7, including crimping the pre-opened stent onto the balloon while maintaining the balloon under vacuum.

9. The method of claim 7, including selecting a stent with a length smaller than the length of the balloon, and crimping the stent onto the balloon so that the ends of the balloon project beyond the ends of the stent for distension of the ends of the balloon under partial inflation.

10. The method of claim 7, including selecting a stent fabricated from a single open-ended tube having a multiplicity of holes in a symmetrical pattern through the tube wall defining a plurality of struts bounding said holes in longitudinally repeating serpentine patterns with notches at intersections of the struts.

11. The method of claim 10, including selecting a stent with struts having one of an oval or erythrocyte cross-sectional shape.

12. A stent delivery system for a vascular or endoluminal stent, comprising:

a balloon catheter; and a metallic stent fabricated from a single open-ended tube, crimped snugly onto a balloon of said catheter between the ends of the balloon; said stent having been opened, before crimping onto the balloon, to a diameter intermediate the diameter of the original tube from which the stent is fabricated and the projected diameter of the stent when fully deployed in a vessel or tract of a patient.

13. The stent delivery system of claim 12, wherein said stent has a multiplicity of holes in a symmetrical pattern through the tube wall defining a plurality of struts bounding said holes in longitudinally repeating serpentine patterns with notches at intersections of the struts.

14. The stent delivery system of claim 12, wherein said stent has a multiplicity of holes in a symmetrical pattern through the tube wall defining a plurality of struts bounding said holes, each of said struts having one of an oval or erythrocyte cross-sectional shape.

15. The stent delivery system of claim 12, wherein the inner diameter of said tube wall is uniform throughout and the outer diameter of said tube wall is tapered from its mid-section to its ends to render the ends of the stent more flexible than its mid-section.

16. The stent delivery system of claim 12, wherein said stent has a length sufficiently less than the length of the balloon so that the ends of the balloon project beyond the ends of the stent to enable distension of the ends of the balloon under partial inflation.

* * * * *